United States Patent
Cadran et al.

(10) Patent No.: US 11,213,802 B2
(45) Date of Patent: *Jan. 4, 2022

(54) MESOPOROUS MIXED OXIDE CATALYST COMPRISING SILICON

(71) Applicants: IFP Energies Nouvelles, Rueil-Malmaison (FR); Compagnie Generale Des Etablissements Michelin, Clermont-Ferrand (FR)

(72) Inventors: Nicolas Cadran, Oullins (FR); Alexandra Chaumonnot, Lyons (FR); Arnold Lambert, Chavanay (FR)

(73) Assignees: IFP Energies Nouvelles, Rueil-Malmaison (FR); Compagnie Generale Des Etablissements Michelin, Clermont-Ferrand (FR)

( * ) Notice: Subject to any disclaimer, the term of this patent is extended or adjusted under 35 U.S.C. 154(b) by 801 days.

This patent is subject to a terminal disclaimer.

(21) Appl. No.: 15/744,106

(22) PCT Filed: Jul. 5, 2016

(86) PCT No.: PCT/EP2016/065821
§ 371 (c)(1),
(2) Date: Jan. 12, 2018

(87) PCT Pub. No.: WO2017/009105
PCT Pub. Date: Jan. 19, 2017

(65) Prior Publication Data
US 2018/0200694 A1    Jul. 19, 2018

(30) Foreign Application Priority Data

Jul. 13, 2015   (FR) ...................... 1556664

(51) Int. Cl.
| | |
|---|---|
| *B01J 21/08* | (2006.01) |
| *B01J 37/03* | (2006.01) |
| *B01J 37/10* | (2006.01) |
| *B01J 23/20* | (2006.01) |
| *B01J 35/10* | (2006.01) |
| *B01J 37/02* | (2006.01) |
| *C07C 1/20* | (2006.01) |
| *B01J 37/08* | (2006.01) |
| *B01J 23/06* | (2006.01) |
| *B01J 23/68* | (2006.01) |
| *B01J 23/847* | (2006.01) |

(52) U.S. Cl.
CPC .............. *B01J 21/08* (2013.01); *B01J 23/20* (2013.01); *B01J 35/1023* (2013.01); *B01J 35/1047* (2013.01); *B01J 35/1061* (2013.01); *B01J 37/0201* (2013.01); *B01J 37/036* (2013.01); *B01J 37/08* (2013.01); *B01J 37/10* (2013.01); *C07C 1/20* (2013.01); *B01J 23/06* (2013.01); *B01J 23/682* (2013.01); *B01J 23/847* (2013.01); *B01J 2523/00* (2013.01); *B01J 2523/27* (2013.01); *B01J 2523/41* (2013.01); *B01J 2523/57* (2013.01); *C07C 2521/08* (2013.01); *C07C 2523/06* (2013.01); *C07C 2523/20* (2013.01)

(58) Field of Classification Search
CPC . B01J 21/08; B01J 37/08; B01J 37/036; B01J 37/10; B01J 23/20; B01J 35/1023; B01J 35/1047; B01J 35/1061; B01J 37/0201; B01J 2523/00; B01J 2523/27; B01J 2523/41; B01J 2523/57; B01J 23/06; B01J 23/682; B01J 23/847; C07C 1/20; C07C 2521/08; C07C 2523/06; C07C 2523/20
See application file for complete search history.

(56) References Cited

U.S. PATENT DOCUMENTS

| | | | |
|---|---|---|---|
| 2,436,125 A | 2/1948 | Spence | |
| 6,107,236 A * | 8/2000 | Pecoraro | ................. B01J 21/08 |
| | | | 502/233 |
| 2004/0030214 A1* | 2/2004 | Schindler | ................ C07C 5/325 |
| | | | 585/660 |

FOREIGN PATENT DOCUMENTS

| | | |
|---|---|---|
| KR | 2011117953 A | 10/2011 |
| WO | 2013125389 A1 | 8/2013 |

OTHER PUBLICATIONS

Debecker et al., "Mesoporous mixed oxide catalysts via non-hydrolytic sol-gel: A review," Applied Catalysis A: General vol. 451, Jan. 31, 2013, 192-206. (Year: 2013).*
Sushkevich et al., "Ethanol conversion into butadiene over Zr-containing molecular sieves doped with silver," Green Chem., 2015, 17, 2552. Published Feb. 16, 2015. (Year: 2015).*
International Search Report PCT/EP2016/065821 dated Oct. 7, 2016.
B. B. Corson et al: "Butadiene from Ethyl Alcohol. Catalysis in the One-and Two-Stop Processes.", Industrial & Engineering Chemistry, vol. 42, No. 2, Feb. 1950 (Feb. 1, 1950), pp. 359-373, XP055051002, ISSN: 0019-7866.
Matthew D. Jones et al: "Investigations into the conversion of ethanol into 1,3-butadiene", Catalysis Science & Technology, vol. 1, No. 2, Feb. 14, 2011 (Feb. 14, 2011), pp. 267, XP055089320, ISSN: 2044-4753.
Maria Suzana P Francisco et al: "Local order structure and surface acidity properties of a Nb2O5/SiO2 mixed oxide prepared by the sol-gel processing method", Journal of Solid State Chemistry, vol. 177, No. 7, Jul. 2004 (Jul. 1, 2004), US, pp. 2432-2439, XP055272923, ISSN: 0022-4596.

(Continued)

*Primary Examiner* — Anthony J Zimmer
(74) *Attorney, Agent, or Firm* — Millen, White, Zelano and Branigan, P.C.; Harry B. Shubin (57) ABSTRACT

A mesoporous mixed oxide catalyst that comprises silicon and at least one metal M that is selected from the group that consists of the elements of groups 4 and 5 of the periodic table and mixtures thereof, with the mass of metal M being between 0.1 and 20% of the mixed oxide mass.

12 Claims, 1 Drawing Sheet

(56) References Cited

OTHER PUBLICATIONS

Cimpeanu et al: "Selective oxidation of a pyrimidine thioether using supported tantalum catalysts", Journal of Catalysis, Academic Press, Duluth, MN, US, vol. 235, No. 1, Oct. 2005 (Oct. 1, 2005), pp. 184-194, XP005078476, ISSN: 0021-9517.
G. Ennas et al: "Characterization of Iron Oxide Nanoparticles in an $Fe_2O_3$-$SiO_2$ Composite Prepared by a Sol-Gel Method", Chemistry of Materials, vol. 10, No. 2, Feb. 1998 (Feb. 1, 1998), US, pp. 495-502, XP055278430, ISSN: 0897-4756.

* cited by examiner

MESOPOROUS MIXED OXIDE CATALYST COMPRISING SILICON

PRIOR ART

Butadiene is widely used in the chemical industry, in particular as a reagent for the production of polymers. Currently, butadiene is almost entirely produced from steam-cracking units, of which it constitutes an upgradable by-product. The price fluctuation of petroleum and the ever-increasing demand for this chemical intermediate product made its price very volatile, which means that an effort should be made to diversify supply means. It is thus well known to one skilled in the art that 1,3-butadiene can be produced starting from ethanol. Two methods have been industrialized on a large scale: the "S. K. Process" and the "Carbide Process." In the "S. K. Process," 1,3-butadiene is produced from ethanol in one step, whereas in the "Carbide Process," 1,3-butadiene is produced in two steps: ethanol is first converted into acetaldehyde, and then an ethanol-acetaldehyde mixture is converted into 1,3-butadiene. The main distinction between the catalysts involved in these methods is that one (S.K. Process) is able to dehydrogenate ethanol into acetaldehyde while producing butadiene from the mixture that is thus formed whereas the other is not able to do so, hence the necessity for a first dehydrogenation step on a specific catalyst. The chemical elements that constitute the catalyst that are the most effective for this method for producing butadiene are magnesium, tantalum, zirconium, hafnium, with butadiene selectivities between 50 and 69%, with niobium (or columbium) being considered as an element that is not very attractive with selectivities of less than 40% (B. B. Corson, H. E. Jones, C. E. Welling, J. A. Hinckley, E. E. Stahly *Ind. Eng. Chem.*, 1950, 42 (2), pp. 359-373).

Regardless of the method (one or two steps), the overall balance of the main reaction is written as follows:

$$2CH_3CH_2OH \rightarrow CH_2CHCHCH_2 + H_2 + 2H_2O$$

Underlying this overall balance are numerous chemical reactions that comprise a dehydrogenation reaction that makes it possible to generate acetaldehyde (I), a reaction for aldolization/crotonization of acetaldehyde into crotonaldehyde (II), a Meerwein-Ponndorf-Verley (MPV) reaction between ethanol and crotonaldehyde (III) and finally a step for dehydration of crotylic alcohol into butadiene (IV).

$$CH_3CH_2OH \rightleftharpoons CH_3CHO + H_2 \quad \text{I}$$

$$2CH_3CHO \rightleftharpoons CH_3CHCH-CHO + H_2O \quad \text{II}$$

$$CH_3CHCH-CHO + CH_3CH_2OH \rightleftharpoons CH_3CHCH-CH_2OH + CH_3CHO \quad \text{III}$$

$$CH_3CHCH-CH_2OH \rightarrow CH_2CHCHCH_2 + H_2O \quad \text{IV}$$

This multiplicity of chemical reactions is at the origin of numerous by-products if the linking of steps is not done in the order specified above, with in particular the presence of secondary condensation and dehydration reactions. In addition, other reactions can take place (such as isomerization, cyclization, the Diels-Alder reaction, etc.), also increasing the number of by-products. In this stage, note that, depending on the nature of the catalyst used for the transformation of ethanol (or of the ethanol-acetaldehyde mixture) into 1,3-butadiene, the distribution of said by-products can greatly vary. Thus, the addition of an acidic element will increase the production of dehydration products (for example, ethylene or diethyl ether), while the addition of a basic element will promote the formation of multiple condensation products (for example, hexenes or hexadienes).

Consequently, regardless of the method (one or two steps), the selectivity of the transformation of ethanol (or of the ethanol-acetaldehyde mixture) into 1,3-butadiene is moderate. However, because of the relatively high price of the raw material, the economic study of the method shows that the effectiveness of the transformation of the feedstock constitutes a significant lever for ensuring its viability. Numerous efforts have therefore been made to maximize this selectivity.

In particular, during the development of the method for producing butadiene from an ethanol/acetaldehyde mixture (two-step method), the best catalyst found was a tantalum oxide deposited on an amorphous silica (*Ind. Eng. Chem.*, 1949, 41, pp. 1012-1017). The selectivity of butadiene was 69% for an initial conversion of the feedstock of 34%. It was also shown that the use of this same catalyst in a "Carbide" industrial unit led to the formation of the following majority impurities (by-products): diethyl ether (23% by weight of impurities), ethylene (11% by weight of impurities), hexenes, hexadienes (11% by weight of impurities), etc. (W. J. Toussaint, J. T. Dunn, D. R. Jackson, *Industrial and Engineering Chemistry*, 1947, 39 (2), pp. 120-125). Despite the presence of by-products, their formation is limited by the relatively weak acido-basicity properties of the tantalum element. The latter also makes it possible to catalyze the reactions II, III and IV very effectively. One of its only drawbacks is in its price.

Actually, according to the report written in 2012 by Jonathan Burla, Ross Fehnel, Philip Louie and Peter Terpeluk of the University of Pennsylvania and entitled "TWO-STEP PRODUCTION OF 1,3-BUTADIENE FROM ETHANOL," the price of silica is around $0.96/lb and that of tantalum around $162/lb. By way of indication, the current prices of niobium and zirconium are around $20/lb and $1/lb, or approximately a price ratio of one order of magnitude between niobium and tantalum and two orders of magnitude between zirconium and tantalum.

Various studies have then been carried out to optimize the effectiveness of tantalum and/or to substitute this element. For example, the application WO 2014/061917 seeks to improve the catalyst based on tantalum via the use of a silicic substrate characterized by mesopores with uniform size and morphology and distributed in a periodic way within the material (so-called mesostructured silica). The U.S. Pat. No. 2,421,361 (W. J. Toussaint, J. T. Dunn, Carbide and Carbon Chemical Corporation, 1947) describes a method for the preparation of butadiene that comprises the transformation of an acyclic mono-olefinic aldehyde (crotonaldehyde or acetaldehyde) and a monohydroxylated alcohol (ethanol) on a catalyst from the group of zirconium oxide, tantalum oxide, niobium oxide, and one of the combinations of these oxides with silica. However, according to the examples that are provided, the tantalum oxide that is used by itself remains the best catalyst for converting the specific ethanol/acetaldehyde mixture. According to *Ind. Eng. Chem.*, 1950, 42 (2), pp. 359-373, the best combinations for the transformation of the ethanol/acetaldehyde mixture are: Ta—Cu, Ta—Zr, Zr—Nb, Zr—Ti and Zr—Th, deposited on a silicic substrate (U.S. Pat. Nos. 2,374,433, 2,436,125, 2,438,464, 2,357,855, 2,447,181). More recently, most of the studies have sought to eliminate tantalum from the catalytic formulation completely, in particular owing to the use of the zirconium or magnesium element:

The application WO 2014/199349 (BASF) uses a Zr, Zn, Cu combination,

The application WO 2014/180778 (Synthos) claims a Zr, Zn, La combination,

The application WO 2014/049158 (Lanxess) uses an Mg—Si mixed oxide that is doped by elements such as Ti, V, Mo, Mn, Cu, Ni, Zn or Cr, The application WO 2013/125389 (Daicel) claims the use of an Mg—Si mixed oxide that is doped by a metal that belongs to the columns 4 to 13, The application WO 2012/015340 (Unisit) uses the combination of an element in the metal state of column 11 and a metal oxide that is selected from among magnesium, titanium, zirconium, tantalum, and niobium.

SUMMARY OF THE INVENTION

The invention relates to a mesoporous mixed oxide catalyst that comprises silicon and at least one metal M that is selected from the group that consists of the elements of groups 4 and 5 of the periodic table and mixtures thereof, with the mass of metal M being between 0.1 and 20% of the mixed oxide mass, with said mixed oxide resulting from the combination of oxygen atoms with at least the silicon element and the element M.

The invention also relates to the use of this catalyst for the production of 1,3-butadiene from a feedstock that comprises at least ethanol at a temperature of between 300 and 400° C., a pressure of between 0.15 and 0.5 MPa, and a volumetric flow rate of between 0.5 and 5 $h^{-1}$.

Advantage of the Invention

This invention describes a method for producing butadiene with a single reactor or with a linking of reactors using a catalyst that comprises—and advantageously consists of—an amorphous mesoporous mixed oxide that comprises the silicon element, at least one metal M selected from the group that consists of the elements of groups 4 and 5 of the periodic table and mixtures thereof, i.e., the periodic table of elements, and optionally at least one metal M' selected from the group that consists of the elements of groups 11 and 12 of the periodic table and mixtures thereof, advantageously a binder, and advantageously an organic adjuvant. One advantage of this invention that uses said catalyst is an improvement in the maintaining of the catalytic performances during the service life of the catalyst, i.e., from one catalytic cycle to the next. Another aspect of the invention is an increase in the number of possible regenerations and therefore of the service life of the catalyst.

DISCLOSURE OF THE INVENTION

The invention relates to a catalyst that comprises—and preferably consists of—an advantageously amorphous, mesoporous mixed oxide, comprising silicon, at least one metal that is selected from the group that consists of the elements of groups 4 and 5 of the periodic table and mixtures thereof, and optionally at least one metal that is selected from the group that consists of the elements of groups 11 and 12 of the periodic table and mixtures thereof, advantageously a binder, and its use as catalyst for the production of butadiene from a feedstock that comprises at least ethanol as well as its preparation method.

Mixed oxide is defined as a solid that results from the combination of oxygen atoms with at least two other elements that are different from the latter, with these elements being linked by a covalent bond. Said mixed oxide comprises at least the silicon element as a first element that is additional to oxygen. Said mixed oxide also comprises at least one metal M that is selected from the group that consists of the elements of groups 4 and 5 of the periodic table and mixtures thereof. The presence of silicon and of the metal M define so-called "binary" mixed oxides, named, for example, Ta—Si, Nb—Si, Zr—Si, etc., in the text below of this invention. It is also possible to combine at least two metals M as defined above in such a way as to obtain mixed oxides with three elements (ternary), with four elements, etc. Preferably, said metal M is selected from the group that consists of tantalum, niobium, zirconium and mixtures thereof. In an even more preferred way, said metal M is selected from the group that consists of tantalum and niobium, taken by itself or in a mixture.

In an optional way, said mixed oxide can also comprise a metal M', in addition to silicon and the metal M. Said metal M' is a metal that is selected from the group that consists of the elements of groups 11 and 12 of the periodic table and mixtures thereof. The presence of silicon, the metal M, and the optional metal M' define so-called "ternary" mixed oxides, named, for example, Ta—Si—Ag, Nb—Si—Zn, etc., in the text below of this invention. It is also possible to combine at least two metals M' as defined above in such a way as to obtain mixed oxides with four elements, etc. Preferably, said metal M' is selected from the group that consists of silver, copper, zinc, and mixtures thereof.

Said mixed oxide comprises at least one M, with the mass of said metal M being between 0.1 and 20%, preferably between 0.3 and 10%, in a preferred way between 0.5 and 5%, and in a very preferred manner between 0.5 and 2% of the mixed oxide mass.

Said mixed oxide advantageously comprises a metal M', with the mass of metal M', when the former is present, being between 0.1 and 20%, preferably between 0.3 and 10%, in a preferred way between 0.5 and 5%, and in a very preferred manner between 0.5 and 2% of the mixed oxide mass.

Mixed oxide comprising an element A, with the mass of the element A being between—or representing between—x and y % of the mixed oxide mass, is defined as said mixed oxide comprising between x and y parts by weight of said element A per 100 parts by weight of said mixed oxide.

Said mixed oxide is mesoporous, i.e., it is characterized by the presence of pores whose size varies between 2 and 50 nm according to the IUPAC classification (K. S. W. Sing, D. H. Everett, R. A. Haul, L. Moscou, J. Pierotti, J. Rouquerol, T. Siemieniewska, *Pure Appl. Chem.*, 1985, 57, 603). In addition to being mesoporous, said mixed oxide can be mesostructured (i.e., can have mesopores of uniform size and distributed in a periodic way in the matrix) or else have hierarchized porosity (presence of micropores and/or macropores in addition to mesopores). In a preferred way, said mixed oxide is mesoporous with unorganized porosity and no micropores. Particularly advantageous results are obtained via the use of a mixed oxide that has a specific surface area of at least 250 $m^2/g$, in a preferred way a specific surface area of at least 400 $m^2/g$ and in an even more preferred way a specific surface area of at least 600 $m^2/g$. Likewise, the pore volume of said mixed oxide is preferably at least 1 ml/g and in a more preferred way at least 1.3 ml/g. In addition, the mean diameter of the pores (or size of the pores) of said mixed oxide is preferably at least 4 nm, in a preferred way between 4.5 and 17 nm, and in an even more preferred way between 4.5 and 10 nm.

The catalyst according to the invention can advantageously comprise at least one porous oxide material that has the role of binder so as to generate the physical properties of the catalysts that are suited to the method (mechanical strength, resistance to attrition, etc.).

Said porous oxide material is preferably a porous oxide material that is selected from the group that is formed by silica, magnesia, clays, titanium oxide, lanthanum oxide, cerium oxide, boron phosphates, and mixtures of at least two of the oxides cited above. It is also possible to use titanates, for example the titanates of zinc, nickel, cobalt. It is also possible to use simple, synthetic or natural clays of the 2:1 dioctahedral phyllosilicate type or the 3:1 trioctahedral phyllosilicate type such as kaolinite, antigorite, chrysotile, montmorillonnite, beidellite, vermiculite, talc, hectorite, saponite, laponite. These clays can optionally be delaminated. The various mixtures that use at least two of the compounds cited above are also suitable for ensuring the binder role.

In a very preferred way, the binder that is used has a silicic nature. For example and in a non-exhaustive way, said silicic binder can be in the form of colloidal solutions or powders.

Preferably, said catalyst comprises 5 to 60% by weight, and in a preferred manner between 10 and 30% by weight, of silicic binder, with the percentages by weight being expressed in relation to the total mass of said catalyst.

The above-cited textural parameters are determined by the analytical technique called "nitrogen volumetric analysis" that corresponds to the physical adsorption of nitrogen molecules in the porosity of the material via a gradual increase in pressure at constant temperature. Specific surface area is defined as the B.E.T. specific surface area ($S_{BET}$ in $m^2/g$) that is determined by nitrogen adsorption in accordance with the ASTM D 3663-78 standard established from the BRUNAUER-EMMETT-TELLER method described in the periodical "*The Journal of American Society,*" 1938, 60, 309. The pore distribution that is representative of a mesopore population is determined by the Barrett-Joyner-Halenda (BJH) model. The nitrogen adsorption-desorption isotherm according to the BJH model that is thus obtained is described in the periodical "*The Journal of American Society,*" 1951, 73, 373, written by E. P. Barrett, L. G. Joyner and P. P. Halenda. The pore volume V is defined as the value that corresponds to the volume that is observed for the partial pressure $P/P^0_{max}$ of the nitrogen adsorption-desorption isotherm. In the following disclosure, the diameter of the mesopores $\phi$ of the mixed oxide according to the invention is determined by the formula $4000 \cdot V/S_{BET}$.

To ensure the catalytic performances of the catalyst according to the invention, the textural properties of said mixed oxide should be controlled as well as possible (to ensure a proper diffusion of the reagents and reaction products), just like the surface reactivity (nature, force and number of active sites), by acting simultaneously on the chemical composition and the degree of homogeneity of said mixed oxide (preferred formation of M-O—Si bonds, with M=metal, O=oxygen and Si=silicon). Consequently, said catalyst can be prepared by any methods that are known to one skilled in the art, making possible the above-mentioned control. In particular, the synthesis methods for obtaining these solids can be inorganic "traditional" synthesis methods (precipitation, gelling from salts) or "modern" metallo-organic methods (precipitation, gelling from alkoxides), with these methods able to be called "sol-gel" methods in a simplified way. These "sol-gel" methods are based on chemical reactions of hydrolysis (and even complexing) and condensation of molecular precursors (salts or alkoxides), performed most often at atmospheric pressure and ambient temperature in an aqueous or aquo-organic medium. It is also possible to use "sol-gel" methods combined with the use of specific synthesis methods such as spray-drying (also called atomization), dip-coating, etc. These synthesis methodologies, in comparison to other conventional methods, make it possible to better control the purity, the chemical composition, the homogeneity and the texture of mesoporous oxides. Preferably, the preparation method that is used for synthesizing the catalyst according to the invention is the metallo-organic modern sol-gel path by precipitation/gelling that comprises at least the following steps:

(a) Dissolution of at least one alkoxide precursor of formula $Si(OR)_{4-a}R'_a$ where R=H, methyl, ethyl and R' is an alkyl chain or a functionalized alkyl chain of the element Si in aqueous, organic or aquo-organic medium (preferably aquo-alcoholic), optionally in the presence of an acid or a base, so as to form an optionally colloidal solution, (b) Addition to the solution that is obtained during the operation (a) of at least one precursor of the metal M, in the pure state or dissolved in a suitable medium that is compatible with said solution that is obtained from the operation (a). The operation (b) can be repeated as many times as necessary, in particular during the addition of separate elements M, which occurs at different times (ternary systems, quaternary systems, etc.), (c) Precipitation of the Si-based mixed oxide, at least the metal M by the addition of an acid, a base, or by application of a specific reaction temperature, (d) Filtration followed by optional washing cycles or evaporation of the suspension that is obtained during the operation (c), (e) At least one heat treatment, advantageously hydrothermal treatment, of the mixed oxide that is obtained in step (d) (drying and/or calcination, and/or steaming, etc.) so as to obtain the catalyst that is used according to the invention. Preferably, the mixed oxide that is obtained at the end of step d) is dried and then calcined. The drying step can be carried out in an oven in a temperature range of 20 to 200° C., preferably 50° C. to 150° C., and in a preferred manner 100° C. to 130° C. during a period of less than 72 hours and preferably less than 24 hours. The calcination step can be carried out in air in an oven in a temperature range of 300 to 800° C., in a preferred way from T=450° C. to T=700° C., and in an even more preferred way from T=540° C. to T=700° C. during a period of less than 24 hours and preferably less than 12 hours.

Compatible is defined as said medium not demixing or precipitating when it is brought into contact with the solution that is obtained from the operation (a) under the conditions of step (b).

The precursors of the element Si and at least the metal M that are used during the operation (a) can be any compound that comprises the element Si or M and that can release this element in solution in reactive form. Thus, the precursor(s) of at least said metal M is/are advantageously an inorganic salt of said metal M of formula $MZ_n$, (n=3 or 4), with Z being a halogen, the $NO_3$ group, the sulfate group, or a perchlorate. The precursor(s) of at least said metal M that is being considered can also be (an) alkoxide precursor(s) of formula $M(OR)_n$ where R=ethyl, isopropyl, n-butyl, s-butyl, t-butyl, etc., or a chelated precursor such as $M(C_5H_8O_2)_n$, with n=3 or 4. The precursor(s) of at least said metal M that is/are being considered can also be (an) oxide(s) or (a) hydroxide(s) of said metal M. As for the silicic precursor, it is obtained from any silica source and advantageously from a sodium silicate precursor of formula $Na_2SiO_3$, a chlorinated precursor of formula $SiCl_4$, an alkoxide precursor of formula $Si(OR)_4$ where R=H, methyl, ethyl, or a chloroalkoxide precursor of formula $Si(OR)_{4-a}Cl_a$ where R=H, methyl, ethyl, with a being between 0 and 4. The silicic precursor can also advantageously be an alkoxide precursor of formula $Si(OR)_{4-a}R'_a$ where R=H, methyl, ethyl and R' is an alkyl chain or an alkyl chain that is functionalized, for example, by a group of thiol, amino, β diketone, sulfonic acid, with a being between 0 and 4. A preferred silicic precursor is tetraethyl orthosilicate (TEOS).

In a preferred manner, said metal M is not impregnated. In a very advantageous manner, said metal M is incorporated only in step b) of the method for preparation of the catalyst according to the invention.

The catalyst according to the invention can be used in powder form or advantageously shaped in a step f) in the form of balls, pellets, granules, or extrudates (cylinders that may or may not be hollow, multilobed cylinders with 2, 3, 4 or 5 lobes, for example, braided cylinders), or rings, etc., with these shaping operations being carried out by the conventional techniques that are known to one skilled in the art. Preferably, said catalyst according to the invention is obtained at the end of a shaping step f) in the form of extrudates of a size of between 1 and 10 mm. However, it is not ruled out that said materials that are obtained will then be, for example, introduced into a piece of equipment that makes it possible to round their surfaces, such as a bezel or any other piece of equipment that makes it possible to make them spherical in shape.

During the shaping step f), the catalyst according to the invention can optionally comprise, and therefore be mixed with, at least one porous oxide material that has the role of binder so as to generate the physical properties of catalysts that are suited to the method (mechanical strength, resistance to attrition, etc.).

Said porous oxide material is preferably a porous oxide material that is selected from the group that is formed by silica, magnesia, clays, titanium oxide, lanthanum oxide, cerium oxide, boron phosphates, and mixtures of at least two of the oxides cited above. It is also possible to use titanates, for example the titanates of zinc, nickel, cobalt. It is also possible to use simple, synthetic or natural clays of the 2:1 dioctahedral phyllosilicate type or the 3:1 trioctahedral phyllosilicate type, such as kaolinite, antigorite, chrysotile, montmorillonnite, beidellite, vermiculite, talc, hectorite, saponite, laponite. These clays can optionally be delaminated. The various mixtures that use at least two of the compounds cited above are also suitable for ensuring the binder role.

In a very preferred way, the binder that is used has a silicic nature. For example and in a non-exhaustive way, said silicic binder can be in the form of colloidal solutions or powders.

Preferably, said catalyst comprises 5 to 60% by weight, and in a preferred manner between 10 and 30% by weight, of silicic binder, with the percentages by weight being expressed in relation to the total mass of said catalyst.

Optionally, at least one organic adjuvant is also mixed during said shaping step f). The presence of said organic adjuvant facilitates the shaping by extrusion. Said organic adjuvant can advantageously be selected from among methyl cellulose, hydroxypropyl methylcellulose, hydroxyethyl cellulose, carboxymethylcellulose, and polyvinyl alcohol. The proportion of said organic adjuvant is advantageously between 0 and 20% by weight, preferably between 0 and 10% by weight, and in a preferred manner between 0 and 7% by weight, in relation to the total mass of said shaped material.

In this particular case of a shaping of the catalyst according to the invention following the heat treatment step e) of the preparation method, said heat treatment step can be carried out again after shaping.

The optional addition of at least one metal M' that is selected from the group that consists of the elements of groups 11 and 12 of the periodic table and mixtures thereof can be carried out according to all of the methods that are known to one skilled in the art and in any steps for synthesis and/or shaping of said catalyst according to the invention. In addition, the use of at least two separate metals M and optionally M' (ternary systems, quaternary systems, etc.) makes possible the incorporation of at least the metals M or M' in addition to any steps for synthesis and/or shaping of said mixed oxide that is used as a catalyst according to the invention and this by all of the methods that are known to one skilled in the art.

Another object of the invention is the use of the catalyst according to the invention for the conversion of a feedstock that comprises at least ethanol into butadiene, manifesting as advantages of significant performances, in particular by increased stability. The representative conditions for this reaction (conditions for which a better productivity and a better selectivity are observed) are a temperature of between 300 and 400° C., preferably between 320° C. and 380° C., a pressure of between 0.15 and 0.5 MPa, preferably between 0.15 and 0.3 MPa, a volumetric flow rate of between 0.5 and 5 $h^{-1}$, preferably between 1 and 4 $h^{-1}$, and, in the case of the "two-step" method where said feedstock comprises ethanol and acetaldehyde, a ratio by mass of ethanol/acetaldehyde of between 1 and 30, in a preferred manner between 2 and 10. The volumetric flow rate is defined as the ratio between the mass flow rate of the feedstock and the catalyst mass.

The invention is illustrated by means of the following examples.

EXAMPLES

Example 1

Preparation of the Catalyst A Based on 2% Ta/SiO$_2$ (2% by Weight of Ta in Relation to the Silica Mass) that is Obtained by Dry Impregnation of the Tantalum Precursor that is Associated with the Surface of a Davisil 636 Commercial Silica (for Comparison Purposes)

2.68 g of tantalum ethoxide (Ta(OCH$_2$CH$_3$)$_5$) is diluted in 96 ml of ethanol. This solution is quickly added drop by drop and mixed with 60 g of the Davisil 636 silica (SBET≈500 m$^2$/g, Vp≈0.9 ml/g and φ≈7 nm, grain size: 200-500 microns) until wettability of the surface of the latter (dry impregnation) is observed. The solid is then placed in an ethanol-saturated atmosphere for 3 hours, dried at 100° C. for 24 hours. The catalyst A is obtained by calcination of the solid that is dried in air at 550° C. for 4 hours.

Example 2

Preparation of the Mixed Oxide Catalyst Ta—Si B Comprising 2% by Weight of Metal Ta in Relation to the Silica Mass, Obtained via the Metallo-Organic Modern Sol-Gel Path (According to the Invention)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 0.66 g of tantalum ethoxide (Ta(OCH$_2$CH$_3$)$_5$) is then added drop by drop under inert conditions to the preceding mixture. 50 ml of a 14% (by volume) ammonia solution is then added. The operation of the system is disrupted, and a gel forms. 19 ml of ethanol is then added to make possible additional stirring for 3 hours. The final gel is filtered, washed with ethanol, and then dried at 100° C. for 24 hours. The catalyst K is obtained by calcination of the solid that is dried in air at 550° C. for 4 hours. The catalyst B that is obtained is characterized by the following textural data: S$_{BET}$=710 m$^2$/g, Vp=1.42 ml/g and ϕ=11.7 nm.

Example 3

Preparation of the Catalyst C Based on 2% Nb/SiO$_2$ (2% by Weight of Nb in Relation to the Silica Mass) that is Obtained by Dry Impregnation of the Niobium Precursor that is Associated with the Surface of the Davisil 636 Commercial Silica (for Comparison Purposes)

4.24 g of niobium oxalate and pentahydrated ammonium oxalate is diluted in 80 ml of water. This solution is quickly added drop by drop and mixed with 50 g of the Davisil 636 silica (SBET≈500 m$^2$/g, Vp≈0.9 ml/g and ϕ≈7 nm, grain size: 200-500 microns) until wettability of the surface of the latter (dry impregnation) is observed. The solid is then placed in a water-saturated atmosphere for 3 hours, dried at 100° C. for 24 hours. The catalyst C is obtained by calcination of the solid that is dried in air at 550° C. for 4 hours.

Example 4

Preparation of the Mixed Oxide Catalyst Nb—Si D that Comprises 2% by Weight of Metal Nb in Relation to the Silica Mass that is Obtained via the Metallo-Organic Modern Sol-Gel Path (According to the Invention)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 0.96 g of niobium ethoxide Nb(OCH$_2$CH$_3$)$_5$) is then added drop by drop under inert conditions to the preceding mixture. 50 ml of a 14% (by volume) ammonia solution is then added. The operation of the system is disrupted, and a gel forms. 19 ml of ethanol is then added to make possible an additional stirring for 3 hours. The final gel is filtered, washed with ethanol, and then dried at 100° C. for 24 hours. The Nb—SiO$_2$ powder that is obtained is then calcined in air at 550° C. for 4 hours. The catalyst D that is obtained is characterized by the following textural data: S$_{BET}$=790 m$^2$/g, Vp=1.02 ml/g and ϕ=6.7 nm.

Example 5

Preparation of the Catalyst E Based on 1% Zn/2% Ta/SiO$_2$ (1% by Weight of Zn and 2% by Weight of Ta in Relation to the Silica Mass) that is Obtained by Dry Impregnation of the Tantalum and Zinc Precursors that are Associated with the Surface of the Davisil 636 Commercial Silica (for Comparison Purposes)

2.27 g of hexahydrated zinc nitrate is diluted in 80 ml of water. This solution is quickly added drop by drop and mixed with 50 g of the Davisil 636 silica (SBET≈500 m$^2$/g, Vp≈0.9 ml/g and ϕ≈7 nm, grain size: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

1.34 g of tantalum ethoxide (Ta(OCH$_2$CH$_3$)$_5$) is diluted in 96 ml of ethanol. This solution is quickly added drop by drop and mixed with 30 g of the previously prepared solid until wettability of the surface of the latter (dry impregnation) is observed. The solid is then placed in an ethanol-saturated atmosphere for 3 hours, dried at 100° C. for 24 hours. The catalyst E is obtained by calcination of the solid, which is dried in air at 550° C. for 4 hours.

Example 6

Preparation of the Mixed Oxide Catalyst Ta—Si—Zn F that Comprises 1% by Weight of the Metal Zn and 2% by Weight of the Metal Ta in Relation to the Silica Mass that is Obtained, Synthesis of the Mixed Oxide Ta—Si via the Metallo-Organic Modern Sol-Gel Path and Dry Impregnation of Said Mixed Oxide by the Associated Zinc Precursor (According to the Invention)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 0.66 g of tantalum ethoxide (Ta(OCH$_2$CH$_3$)$_5$) is then added drop by drop under inert conditions to the preceding mixture. 50 ml of a 14% (by volume) ammonia solution is then added. The operation of the system is disrupted, and a gel forms. 19 ml of ethanol is then added to make possible an additional stirring for 3 hours. The final gel is filtered, washed with ethanol, and then dried at 100° C. for 24 hours. The catalyst K is obtained by calcination of the solid that is dried in air at 550° C. for 4 hours.

0.91 g of hexahydrated zinc nitrate is diluted in 56 ml of water. This solution is quickly added drop by drop and mixed with 20 g of the mixed oxide Ta—Si (SBET≈710 m$^2$/g, Vp≈1.42 ml/g and ϕ≈11.7 nm) until wettability of the surface of the latter (dry impregnation) is observed. The solid is then placed in a water-saturated atmosphere for 3 hours, dried at 100° C. for 24 hours. The catalyst F is obtained by calcination of the solid, which is dried in air at 550° C. for 4 hours.

Definition of the Terms pph (g/g$_{cat}$h):

$$pph = \frac{\text{mass flow rate of the feedstock } (g/h)}{\text{catalyst mass } (gcat)}$$

Conversion (% by weight):

$$\text{conversion} = 100 * \left(1 - \frac{\text{mass flow rate of exiting ethanol} + \text{mass flow rate of exiting acetaldehyde}}{\text{mass flow rate of entering ethanol} + \text{mass flow rate of entering acetaldehyde}}\right)$$

Productivity ($g_c/g_M/h$)

$$productivity = \frac{\text{mass flow rate of carbon belonging to butadiene } (gc/h)}{\text{catalyst mass } (gM)}$$

Selectivity (% C):

$$selectivity = \frac{\text{mass flow rate of carbon belonging to butadiene } (gc/h)}{\text{mass flow rate of carbon belonging to the converted feedstock}}$$

Description of the Catalytic Test Unit

The reactor that is used in the following examples consists of a stainless steel tube that is 20 cm long and 10 mm in diameter. The reactor is first loaded with carborundum and then with the catalyst that is diluted in carborundum and finally with carborundum. The carborundum is inert relative to the feedstock and does not influence the catalytic results; it makes it possible to position the catalyst in the isothermal zone of the reactor and to limit the risks of material and heat transfer problems. The temperature of the reactor is controlled with a tubular furnace with three heating zones. The liquid feedstock (mixture of ethanol and acetaldehyde in a ratio R) is injected via a double-piston HPLC pump. The liquid stream is evaporated in the lines that are heated by a tracer before entering into the reactor and is homogenized by passing into a static mixer. The products that are formed during the reaction are kept in the vapor phase so that they can be analyzed on-line by gas chromatography (PONA and Carboxen 1010 capillary columns) to make possible the most precise identification of the hundreds of products formed. The catalyst is activated in situ under nitrogen at the test temperature. The specific operating conditions are described in the following examples.

Catalytic Test Protocol

For all of the catalysts that are prepared according to the examples that are described below, the test conditions have been as follows:

The test for transformation of the alcoholic feedstock was carried out at a temperature [sic] at a pressure of 0.15 MPa with a start-up temperature of 340° C. The feedstock flow rate (and therefore the pph) is adjusted for each catalyst so as to obtain initially (at 340° C.) the desired conversion level. The temperature is gradually increased to compensate for the deactivation of the catalyst and to keep a butadiene productivity level stable. The test is stopped from the time when the test temperature exceeds 375° C.

Figure 1:
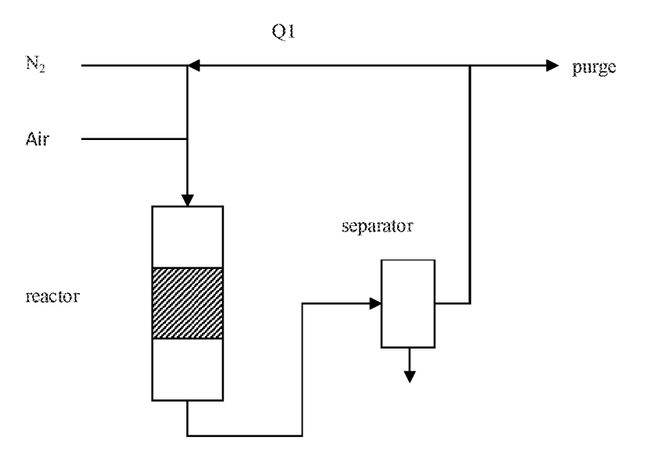
FIG. 1 represents a diagrammatic depiction of the process.

At the end of each test, the catalyst is regenerated by calcination in air. The regeneration conditions were selected so as to be the most representative of industrial regeneration. The conditions of the regeneration step are described in detail in Table 1, and the regeneration is carried out according to the diagram that is shown in FIG. 1, which illustrates the diagrammatic depiction of the circulation of the streams during various phases. After a first period under a stream of nitrogen that makes it possible to evacuate the residues of volatile compounds that are present in the reactor and on the catalyst, air is introduced into the unit to initiate the regeneration of the catalyst. This air is diluted using a partial recycling of the exiting gas (recycling rate=5), gas that consists of an N2, CO2 and H2O mixture as well as the oxygen that has not reacted. During this phase (periods 1-4), the temperature is gradually increased so as to burn the coke while managing the exotherm of the reaction. Finally, the residual coke is burned completely after a last step in pure air (period 5). The unit is then rendered inert under N2 so as to be able to begin the next test.

In a diagrammatic manner, FIG. 1 shows the circulation mode of fluids during the regeneration phase.

TABLE 1

Operating Conditions of the Step for Regenerating Catalysts

| Periods | Initial Temperature | Final Temperature | Rate of Climb | Gas Return Flow Rate Q1 (l/h/gcat) | Nitrogen Flow Rate Q2 (l/h/gcat) | Air Flow Rate Q3 (l/h/gcat) | Duration of the Stage | Phenomenon |
|---|---|---|---|---|---|---|---|---|
| 1 | 200° C. | 350° C. | 20° C./h | 1.4 | 0 | 0.6 | 5 h | Calcination |
| 2 | 350° C. | 480° C. | 20° C./h | 1.4 | 0 | 0.6 | 5 h | of Coke |
| 3 | 480° C. | 540° C. | 20° C./h | 1.4 | 0 | 0.6 | 10 h | Calcination |
| 4 | 540° C. | 590° C. | 20° C./h | 1.4 | 0 | 0.6 | 10 h | of Hard Coke |
| 5 | 580° C. | 590° C. | — | 0 | 0 | 2 | 10 h | |
| 6 | 580° C. | 230° C. | 100° C./h | 1.4 | 0.6 | 0 | 2 h | Rendering Inert |

The catalytic test/regeneration sequence is repeated 20× so as to be able to extrapolate the service life of the catalyst. In the following examples, the former will correspond to the number of cycles that the catalyst can undergo before its productivity level reaches a critical level, set at half its starting level, i.e., on the level of the catalyst that was just prepared.

Example 7

Comparison of the Ta—Si Mixed Oxide Catalyst System and Impregnated Ta/Si Catalyst In this example, the ethanol/acetaldehyde ratio of the feedstock is set at 2.5 mol/mol, the beginning test temperature at 340° C., and the pressure at 0.15 MPa. For each catalyst, the feedstock flow rate is set to obtain a 45% conversion. Maintaining butadiene productivity on the cycle is ensured by a regular increase in the temperature of the reactor. The losses in productivity between each cycle reflect the rate of aging of the catalyst.

| Example | Catalyst | Productivity during the 1st Cycle ($g/g_{Ta}/h$) | Productivity after 20 Cycles ($g/g_{Ta}/h$) | Loss in Productivity after 20 Cycles | Number of Cycles Extrapolated before Reaching Minimum Productivity |
|---|---|---|---|---|---|
| 1- For Comparison Purposes | A- 2% Ta/SiO$_2$ | 37 | 22 | 41% | 21 |
| 2 | B- 2% Ta—SiO$_2$ | 31 | 26 | 16% | 65 |

Example 8

Comparison of the Nb—Si Mixed Oxide Catalyst System and Impregnated Nb/Si Catalyst In this example, the ethanol/acetaldehyde ratio of the feedstock is set at 2.5 mol/mol, the beginning test temperature at 340° C., and the pressure at 0.15 MPa. For each catalyst, the feedstock flow rate is set to obtain a 30% conversion. Maintaining butadiene productivity on the cycle is ensured by a regular increase in the temperature of the reactor. The losses in productivity between each cycle reflect the rate of aging of the catalyst.

| Example | Catalyst | Productivity during the 1st Cycle ($g/g_{Nb}/h$) | Productivity after 20 Cycles ($g/g_{Nb}/h$) | Loss in Productivity after 20 Cycles | Number of Cycles Extrapolated before Reaching Minimum Productivity |
|---|---|---|---|---|---|
| 1- For Comparison Purposes | C- 2% Nb/SiO$_2$ | 30 | 12 | 60% | 15 |
| 2 | D- 2% Nb—SiO$_2$ | 22 | 18 | 18% | 70 |

Example 9

Comparison of the Ta—Si—Zn Mixed Oxide Catalyst System and Impregnated Ta/Zn/Si Catalyst In this example, the ethanol/acetaldehyde ratio of the feedstock is set at 24 mol/mol, the beginning test temperature at 340° C., and the pressure at 0.15 MPa. For each catalyst, the feedstock flow rate is set to obtain a 55% conversion. Maintaining butadiene productivity on the cycle is ensured by a regular increase in the temperature of the reactor. The losses in productivity between each cycle reflect the rate of aging of the catalyst.

| Example | Catalyst | Productivity during the 1st Cycle ($g/g_{Ta}/h$) | Productivity after 20 Cycles ($g/g_{Ta}/h$) | Loss in Productivity after 20 Cycles | Number of Cycles Extrapolated before Reaching Minimum Productivity |
|---|---|---|---|---|---|
| 1- For Comparison Purposes | E- 1% Zn/2% Ta/SiO$_2$ | 12 | 8 | 33% | 30 |
| 2 | F- 1% Zn-2% Ta—SiO$_2$ | 11 | 10 | 10% | 100 |

In Examples 7 to 9, it is observed that the mixed catalyst oxide according to the invention has a better stability than the catalyst that has a similar formulation, but for which the active phase has been deposited on the substrate.

The invention claimed is:

1. A catalyst comprising a mesoporous mixed oxide that comprises silicon and at least one metal M that is selected from the group consisting of tantalum, niobium, zirconium, and mixtures thereof, with the mass of metal M being between 0.1 and 20% of the mixed oxide mass, with said mixed oxide being a solid mixed oxide of both silicon and metal M, having M-O—Si bonds, said mixed oxide having a specific surface area of at least 600 m$^2$/g, a pore volume of at least 1 ml/g and a mean diameter of the pores of between 4.5 and 17 nm, the specific surface area being a B.E.T. specific surface area that is determined by nitrogen adsorption in accordance with the ASTM D 3663-78 standard established from the BRUNAUER-EMMETT-TELLER method, the pore volume V corresponding to the volume that is observed for the partial pressure $P/P^0_{max}$ of the nitrogen adsorption-desorption isotherm determined by the Barrett-Joyner-Halenda model, the diameter of the mesopores φ being determined by the formula $4000 \cdot V/S_{BET}$.

2. The catalyst according to claim 1, further comprising a metal M', with said metal M' being a metal that is selected from the group consisting of the elements of groups 11 and 12 of the periodic table and mixtures thereof, with the mass of metal M' being between 0.1 and 20% of the mixed oxide mass.

3. The catalyst according to claim 2, in which said metal M' is selected from the group consisting of silver, copper, zinc and mixtures thereof.

4. The catalyst according to claim 1, in which said mixed oxide is mesostructured.

5. The catalyst according to claim 1 that is shaped in the form of balls, pellets, granules, or extrudates, or rings.

6. The catalyst according to claim 5, further comprising at least one porous oxide material that has the role of a binder, with said porous oxide material being silica, magnesia, clays, titanium oxide, lanthanum oxide, cerium oxide, boron phosphates, or mixtures of at least two of the oxides.

7. A method for preparation of the catalyst according to claim 1 via metallo-organic modern sol-gel by precipitation/gelling that comprises at least the following:
(a) dissolution of at least one alkoxide precursor of formula $Si(OR)_{4-a}R'_a$, where R=H, methyl, ethyl and R' is an alkyl chain or a functionalized alkyl chain of the element Si in aqueous, organic or aquo-organic medium, optionally in the presence of an acid or a base, so as to form an optionally colloidal solution,
(b) addition to the solution that is obtained during (a) of at least one precursor of the metal M, in the pure state or dissolved in a suitable medium with said solution that is obtained from the operation (a), such that said medium does not demix or precipitate when it is brought into contact with the solution obtained from (a) under the conditions of (b),
(c) precipitation of the Si-based mixed oxide, at least the metal M by the addition of an acid, a base, or by application of a specific reaction temperature,
(d) filtration followed by optional washing cycles or evaporation of the suspension that is obtained during (c),
(e) at least one heat treatment of mixed oxide that is obtained in (d) so as to obtain said catalyst.

8. The method for preparation of the catalyst according to claim 7, in which said heat treatment (e) is drying followed by calcination, with said drying being carried out in an oven in a temperature range of 20 to 200° C. during a period of less than 72 hours, with said calcination being carried out in air in an oven in a temperature range of 300 to 800° C. during a period of less than 24 hours.

9. A process for the production of 1,3-butadiene from a feedstock that comprises at least ethanol, comprising contacting said feedstock with a catalyst according to claim 1, at a temperature of between 300 and 400° C., a pressure of between 0.15 and 0.5 MPa, and a volumetric flow rate of between 0.5 and 5 $h^{-1}$.

10. The process according to claim 9, in which the temperature is between 320° C. and 380° C.

11. The process according to claim 9, in which the pressure is between 0.15 and 0.3 MPa.

12. The process according to claim 9, in which the volumetric flow rate is between 1 and 4 $h^{-1}$.

* * * * *